United States Patent [19]

Bolduc et al.

[11] 3,972,331

[45] Aug. 3, 1976

[54] DISPENSING CATHETER

[75] Inventors: Lee R. Bolduc, Minneapolis; Eugene A. Dickhudt, St. Paul, both of Minn.

[73] Assignee: Population Research Incorporated, Minneapolis, Minn.

[22] Filed: Jan. 24, 1975

[21] Appl. No.: 543,877

Related U.S. Application Data

[63] Continuation of Ser. No. 339,911, March 9, 1973, abandoned.

[52] U.S. Cl. ............................ 128/232; 128/235; 128/349 B; 128/1 R
[51] Int. Cl.² ............................................ A61M 1/00
[58] Field of Search ......... 128/232, 224, 234, 240, 128/241, 246, 260, 216, 349, 127, 129, 1 R, 218, 303, 341, 130, 235

[56] References Cited
UNITED STATES PATENTS

| | | | |
|---|---|---|---|
| 2,696,212 | 12/1954 | Dunmire | 128/216 |
| 2,699,167 | 1/1955 | Raiche | 128/216 |
| 2,854,982 | 10/1958 | Pagano | 128/349 BV |
| 3,042,030 | 7/1962 | Read | 128/127 |
| 3,211,151 | 10/1965 | Foderick et al. | 128/349 B |
| 3,394,705 | 7/1968 | Abramson | 128/349 B |
| 3,401,689 | 9/1968 | Greenwood | 128/129 |
| 3,422,813 | 1/1969 | Braley, Jr. et al. | 128/1 |
| 3,452,749 | 7/1969 | Riedell | 128/129 |
| 3,459,175 | 8/1969 | Miller | 128/349 B |
| 3,680,542 | 8/1972 | Cimber | 128/1 R |
| 3,721,229 | 3/1973 | Panzer | 128/2 A |
| 3,805,767 | 4/1974 | Erb | 128/1 R |
| 3,817,248 | 6/1974 | Buckles et al. | 128/260 |

OTHER PUBLICATIONS

The Effect of Methyl Cyanoacrylate Tissue Adhesive on the Human Fallopian Tube and Endometrium by Stevenson et al., Journal of Obstetrics and Gynaecology of the British Commonwealth, Nov. 1972, vol. 79, pp. 1028–1039.
Human Sterilization, Richart et al., 1972, pp. 101–115 and 353–359.

*Primary Examiner*—John D. Yasko
*Attorney, Agent, or Firm*—Lew Schwartz; Wayne A. Sivertson

[57] ABSTRACT

An intrauterine catheter attached to a fluid dispensing unit for injecting fluids, as drug materials, into the canal of the Fallopian tube. The catheter is an elongated tubular member having a pair of isolated tubes. A first of the tubes has an expandable balloon on its outer end for substantially completely filling a uterine cavity when expanded. The dispensing unit has a housing with chambers. Containers storing the drug material and fluid are located in the chambers. The containers are collapsible hollow bodies which are pierced by needles which carry the fluids to the tubular member. Plungers collapse the containers to drive the needles through the container walls whereby the fluid in the containers is discharged into the tubes of the catheter. A hand operated actuator is operable to sequentially dispense fluid from a first container into the first tube and then a second container into the other tube.

50 Claims, 31 Drawing Figures

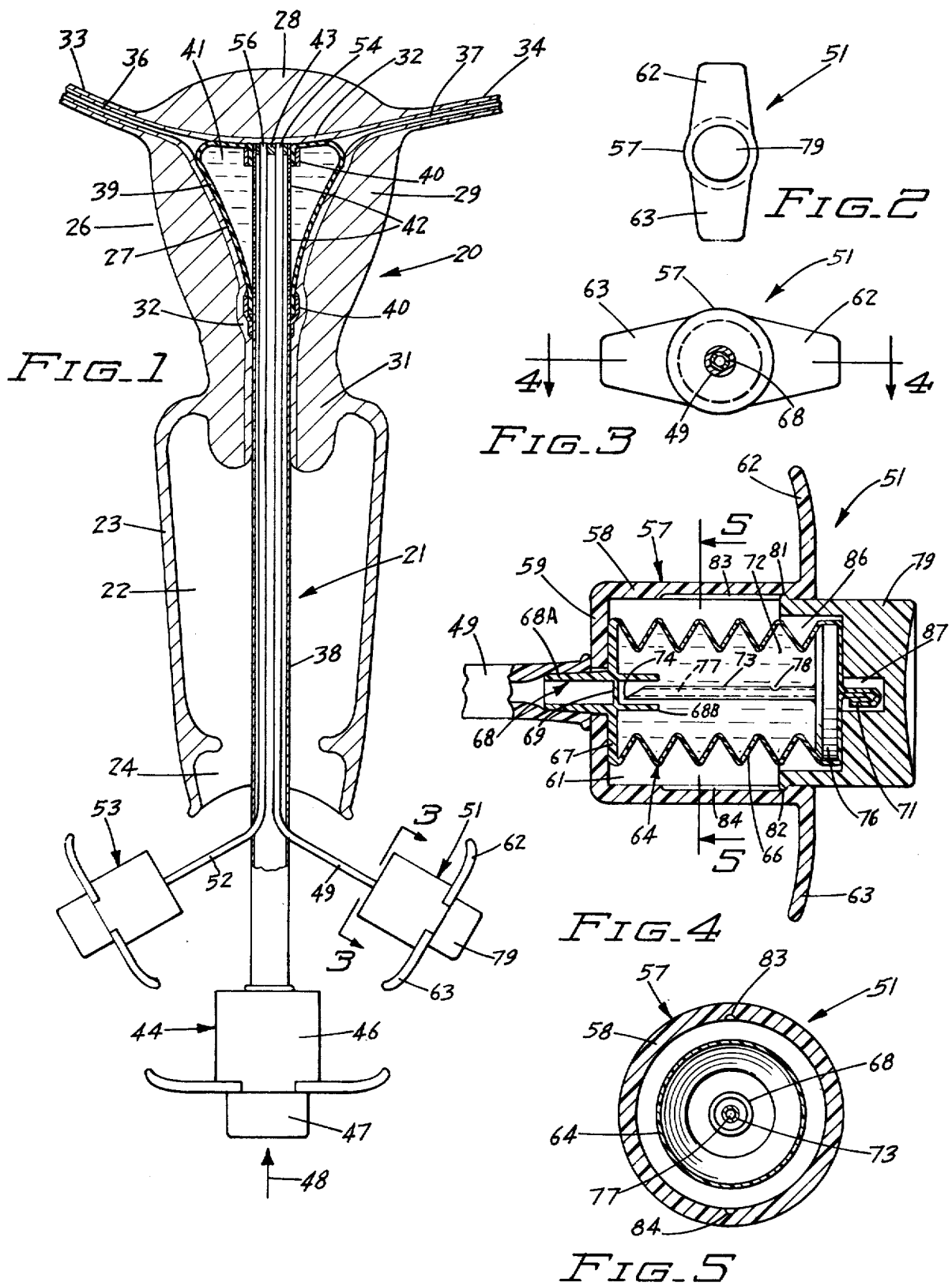

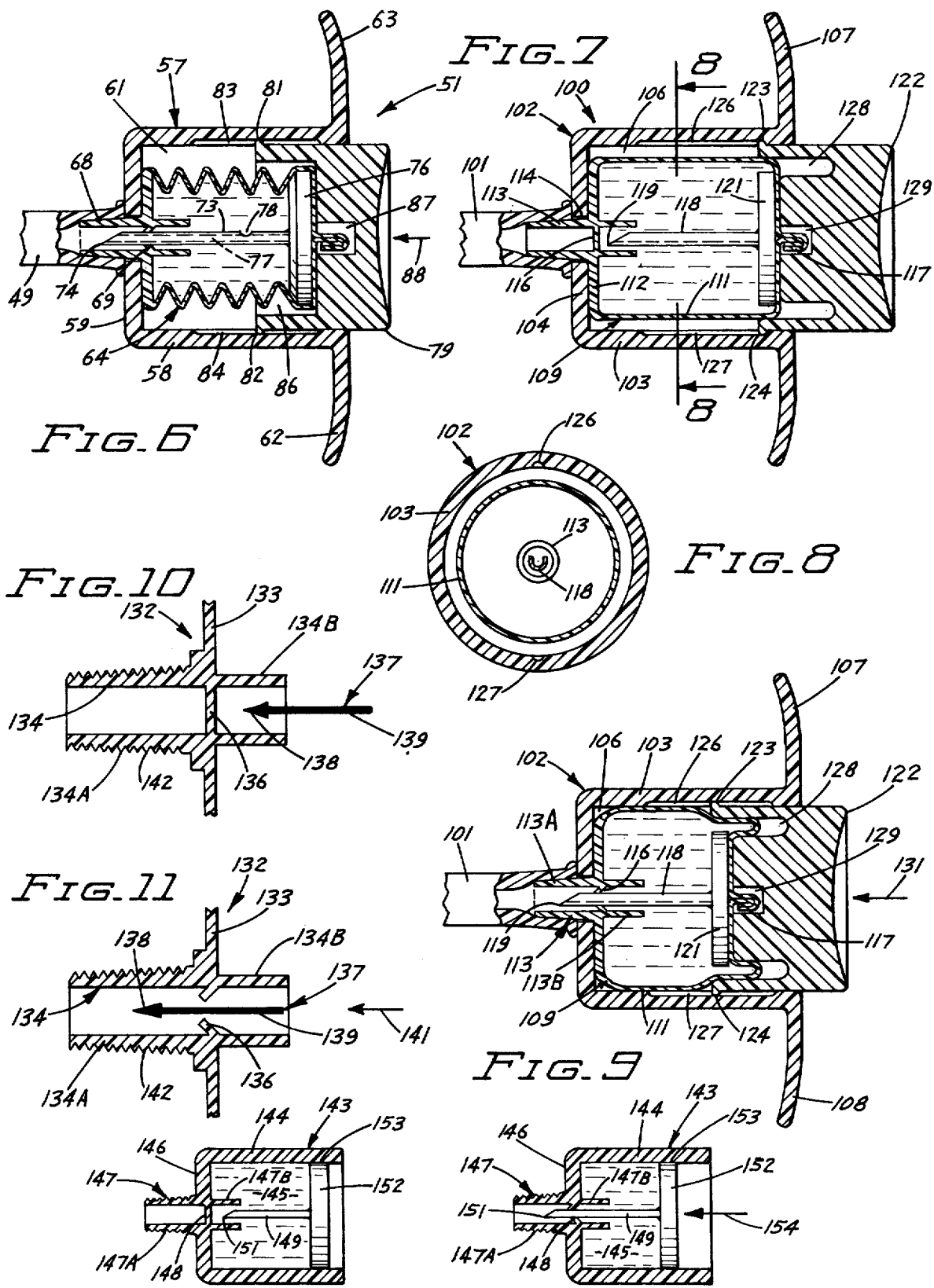

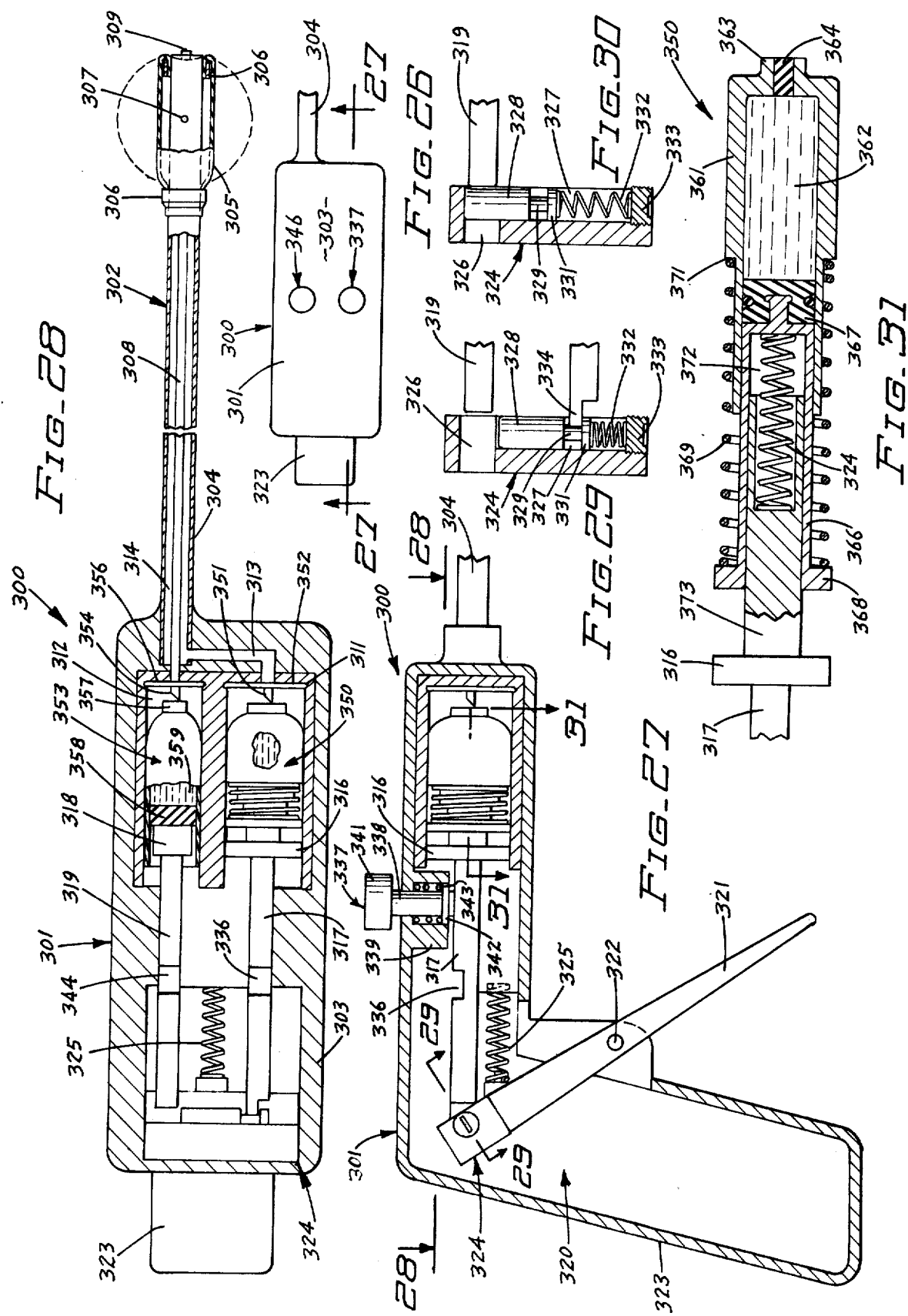

DISPENSING CATHETER

RELATED CASES

This application is a continuation of Ser. No. 339,911, filed Mar. 9, 1973, entitled: "Dispensing Catheter" now abandoned.

BACKGROUND OF THE INVENTION

Bilateral disection of Fallopian tubes is a common surgical procedure to sterilize a female primate. This procedure involves severing and tying the Fallopian tubes. Intrauterine devices as plugs and wires are used to temporarily sterilize a female. These devices include plugs which are inserted into the canals of the Fallopian tubes to prevent ova from passing through the canal into the uterus. The plugs do not insure that the ova cannot flow through the canal into the tube. The plugs can be dislodged and lost without the female being aware of it. There is no assurance that the plug devices are effective. Cimber in U.S. Pat. Nos. 3,675,639 and 3,680,542 discloses plugs attached to the uterine wall to block the entrance of ova into the uterus from the Fallopian canal and exit of sperm from the uterine cavity into the Fallopian canal. These plugs are designed to effect temporary sterilization in that they can be removed and do not cause permanent blockage of the canal of the Fallopian tubes. The plug contraceptive devices are not entirely effective in that it is possible for ova to by-pass the plugs and enter the uterus.

Liquid tissue adhesives have been developed which polymerize when applied to moist living tissue. The adhesives have been used for various surgical procedures. When the tissue adhesive is used, the cells adjacent the tissue are damaged and eventually replaced with a fibrous tissue. A liquid tissue adhesive has been injected into the uterine cavity with a catheter to occlude the canals of the Fallopian tubes.

The use of balloons to block the lower portion of the uterus when applying liquid tissue adhesives to the Fallopian tubes is also known in the art. See, for example, "The Effect of Methyl Cyanoacrylate Tissue Adhesive on the Human Fallopian Tube and Endometrium," by Stevenson, et al., *The Journal of Obstetrics and Gynaecology of the British Commonwealth*, Nov., 1972, Vol. 79, pp. 1028–1039, *Human Sterilization*, edited by Richart and Prager, 1972 and *Female Sterilization*, edited by Duncan, et al., 1972 (See p. 107 e.g.).

One of the problems with the prior art methods of applying liquid tissue adhesives is that in an attempt to assure occlusion of the Fallopian tubes a large amount of the adhesive often had to be inserted into the uterine cavity. Only a small amount of tissue adhesive entered the Fallopian tubes, so the prior art metehods were not only wasteful of materials, but had the medically undesirable effect of leaving large amounts of material on the endometrium of the uterus.

The apparatus of the present invention overcomes these problems by providing a highly flexible structure which is expanded to completely fill the uterine cavity prior to insertion of the substance for occluding the Fallopian tubes.

SUMMARY OF THE INVENTION

The invention is directed to an apparatus for dispensing a fluid, as a drug, into the canals of the Fallopian tubes. The apparatus has a housing having a chamber. Container means storing the fluid is located in the chamber. Means having a passage for receiving the fluid from the container means is associated with the housing. Means, as a needle is operable to puncture a part of the container means whereby fluid from the container means passes to the passage and the means for receiving the fluid. Actuator means cooperate with the container means and means for piercing the container means whereby fluid within the container means flows from the container means into the passage for receiving fluid.

One form of the container means has a collapsible side wall surrounding a chamber for storing one unit of fluid. The needle is located within the chamber whereby the container means, fluid and needle are a compact assembly with the needle protected by the container means. The bottom wall of the container means has a tubular member closed with a diaphragm. The needle pierces the diaphragm when the container means is collapsed whereby the fluid is dispensed from the container.

One form of the apparatus has a body with a pair of chambers and an elongated first tube adapted to be inserted into the uterine cavity. A second tube within the first tube is connected to one of the chambers. An expandable sleeve attached to the end of the first tube fills the uterine cavity. Fluid, as water or air, under pressure within the sleeve holds the sleeve in firm engagement with the inner wall of the uterus. Containers storing fluids are located in the chambers. An actuator mechanism cooperates with the containers to sequentially dispense the fluids into the first tube to expand the sleeve and then into the second tube to discharge fluid, as a drug, tissue adhesive, or the like, into the uterine cavity.

The invention includes the method of occluding the canals of the Fallopian tubes by inserting a catheter having an expandable sleeve into the uterine cavity through the cervical opening. The expandable sleeve is subjected to fluid under pressure to hold the sleeve in firm uniform engagement with the inner wall of the uterus. A fluid, as a drug, tissue adhesive, or the like, is delivered via the catheter to the upper section of the uterine cavity. The fluid flows over the top of the expanded sleeve and into the canals of the Fallopian tube. Tissue adhesive fluids react with the moisture in the tissue of the Fallopian tube to set up the adhesive thereby blocking the canals. Other types of fluids can be injected into the canals to kill the tissue of the canal linings. This tissue is replaced with scar tissue which occludes the canals. The catheter is removed from the uterine cavity after the sleeve is deflated by draining the fluid therefrom.

IN THE DRAWINGS

FIG. 1 is a longitudinal sectional view of the genital system of a female primate with the dispensing catheter extending into the uterine cavity;

FIG. 2 is a top elevational lview of the dispensing unit of the catheter;

FIG. 3 is an enlarged sectional view taken along line 3—3 of FIG. 1;

FIG. 4 is an enlarged sectional view taken along the line 4—4 of FIG. 3;

FIG. 5 is a sectional view taken along the line 5—5 of FIG. 4;

FIG. 6 is a sectional view similar to FIG. 4 showing the dispensing unit actuated to discharge fluid therefrom;

FIG. 7 is a cross-sectional view of a modified dispensing unit for the catheter dispenser;

FIG. 8 is a sectional view taken along the line 8—8;

FIG. 9 is a sectional view similar to FIG. 7 showing the dispensing unit in the discharge position;

FIG. 10 is a diagrammatic view of a further modification of the dispensing unit in the non-dispensing position;

FIG. 11 is a sectional view similar to FIG. 10 showing the dispensing unit in the discharge position;

FIG. 12 is a longitudinal sectional view of the further modified dispensing unit for the catheter dispenser in the non-dispensing position;

FIG. 13 is a view similar to FIG. 12 showing the dispensing unit in the discharge position;

FIG. 26 is a top plan view of another modification of the dispensing catheter of the invention;

FIG. 27 is an enlarged sectional view taken along the line 27—27 of FIG. 26;

FIG. 28 is a sectional view taken along the line 28—28 of FIG. 27;

FIG. 29 is an enlarged sectional view taken along the line 29—29 of FIG. 27;

FIG. 30 is a view similar to FIG. 29 showing the movable member in the second position; and FIG. 31 is an enlarged sectional view of the fluid container assembly used in the dispensing catheter.

Figure 14:
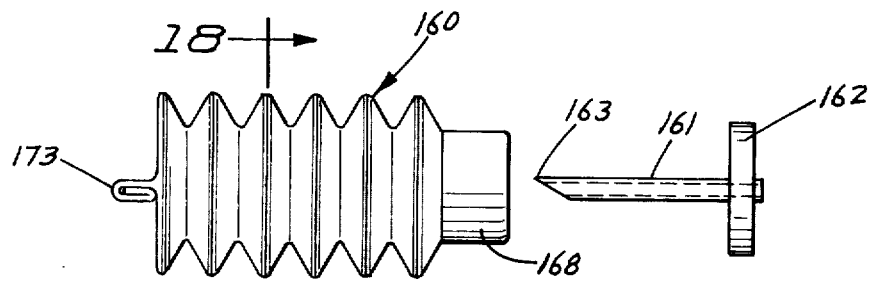
FIG. 14 is a side elevational view of a container spaced from a needle adapted to carry fluid from the container.
Figure 16:
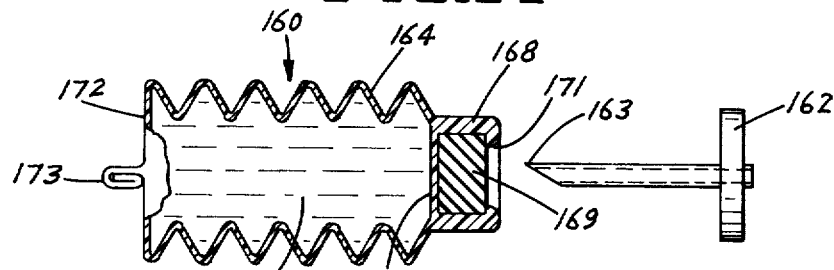
FIG. 16 is a longitudinal sectional view taken along line 16—16 of FIG. 15.
Figure 15:
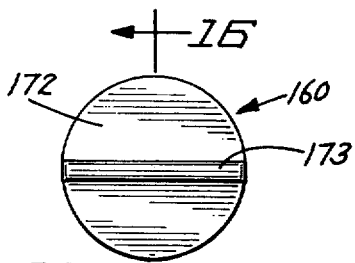
FIG. 15 is an end elevational view of the sealed end of the container of FIG. 14.

Referring to the drawings, there is shown in FIG. 1 a diagrammatic female primate genital system indicated generally at 20. An intrauterine catheter indicated generally at 21 is located in the genital system to direct a fluid, as drugs, tissue adhesive, or other materials, into the canals of the Fallopian tubes. The tissue adhesive can be isobutyl 2-cyonoacrylate monomer, silver nitrate or quinacrine materials. The cyonoacrylate monomer is a liquid plastic which sets up or polymerizes the response to moisture and thereby functions to occlude the canals of the Fallopian tubes. The drug materials can be of the type that temporarily block or occlude the canals of the Fallopian tubes. After a period of time the canals will reopen to resume their normal function.

The genital system 20 has an elongated vagina 22 defined by the cylindrical vaginal wall 23. The vagina 22 opens into the vestibule 24. The opposite end of the vagina is attached to the uterus, indicated generally at 26. Uterus 26 is a pear-shaped, thick walled, hollow organ situated between the bladder and rectum. Uterus 26 has a uterine cavity 27 which is flattened and triangular in shape. The size of the uterine cavity varies from female to female. The top of uterus 26 or fundus 28 is joined to the uterus body 29. The lower end of the body contains the cervix 31 which separates the vigina 22 from the uterine cavity 27. The uterine wall is composed of an outer serosal layer, or peritoneum; a firm, thick, intermediate coate of smooth muscle tissue, or myometrium; and an inner mucosal lining, or endometrium 32.

Leading to the upper part of opposite sides of the uterus 26 are Fallopian tubes 33 and 34. The Fallopian tubes are paired, trumpet-shaped, muscular members which extend from the superior angles of the uterine cavity to the ovaries (not shown). The ovaries are solid, slightly irregular shaped bodies situated on either side of the uterus behind and below the Fallopian tubes.

Fallopian tubes 33 and 34 each have a canal or aqueduct 36 and 37 respectively. The Fallopian tubes are musculomembranous structures about 12 cm in length. They are commonly divided into an isthmus, intramural and ampullary sections. The canals 36 and 37 provide passages for the movement of ova from the ovaries into the uterine cavity. The intramural section of the Fallopian tubes traverses the uterine wall in more or less straight fashion. It has an ampulla-like dilation just before it communicates with the uterine cavity 27. The canals 36 and 37 are narrowest at the intramural sections. The walls of the Fallopian tubes consist of three layers: a serosal layer, a muscular layer and a mucosal lining. The muscular layer includes longitudinal muscle fibers which, when contracted, bring the ends of the Fallopian tubes in close contact with the surface of the ovaries. Blood vessels are abundant in the muscular layer where they form with the muscle bundles a kind of erectile tissue which, if engorged, moves the Fallopian tubes to sweep over the surface of the ovaries. This movement of the Fallopian tubes is impaired when the tubes are severed and tied. The occluding of the canals 36 and 37 with the drug material according to the invention does not interfere with the erectile action and movement of the Fallopian tubes.

Catheter 21 has an elongated first tube 38 having a length sufficient to extend through the vagina and into the uterine cavity 27. An expandable sleeve member 39 as a balloon or the like is secured to the upper end of tube 38 with bands 40. The outer end of sleeve member 39 terminates at the outer end of tube 38. Sleeve member 39 is a flexible elastic member made of relaxed rubber material. The rubber material has uniform surface tension and uniform expansion characteristics. Sleeve member 39 is expanded into uniform and firm engagement with the inner wall of the uterus regardless of the size of the uterine cavity. This enables the same catheter construction to be used on all types of primate females. Expanded sleeve member 39 has a generally pear-shaped chamber 41 filled with fluid, as water, air or the like. The tube 38 has a plurality of holes 42 connecting the passage of tube 38 with the chamber 41. The upper end of tube 39 is closed with a plug 43.

The end of tube 38, projected from the vestibule 24, is attached to a fluid dispensing unit indicated generally at 44. Tube 38 can be releasably attached to dispensing unit 44 or fixed to the dispensing unit 44. The dispensing unit has a body 46 carrying a movable plunger 47. When plunger 47 is moved in the direction of arrow 48, a fluid, is forced from the dispensing unit 44 into the expandable sleeve member 39 to form a closure and fill the uterine cavity 27.

Located within the tube 38 are a pair of smaller tubes 49 and 52 for carrying fluids into the uterine cavity 27. Tube 49 has a portion extended outwardly from the tube 38 and attached to a dispensing unit 51. Tube 52 is attached to a dispensing unit 53. Dispensing unit 51 and 53 are identical in construction and can be used to dispense the same fluids or different fluids at separate time intervals. One of the dispensing units can dispense a neutralizer fluid into the uterine cavity. The following description is limited to dispensing unit 51.

Referring to FIGS. 2 to 5, dispensing unit 51 has a body or housing 57 comprising a cylindrical side wall 58 and an end wall 59. Housing 57 has a chamber 61 and outwardly directed ears 62 and 63. Ears 62 and 63 extend in diametrically opposite directions from opposite sides of the open end of body 57 and cylindrical side wall 58. A collapsible container or ampulla indicated generally at 64 is located in chamber 61. The container holds drug or similar material used in the treatment and/or occlusion of the canals of the Fallopian tubes. The container 64 has an accordion cylindrical side wall 66 secured to a transverse generally flat bottom wall 67. The center portion of bottom wall 67 has longitudinal tubular member 68. Member 68 has an outwardly projected portion 68A and an inwardly directed portion 68B. The tubular member 68 is closed with a transverse diaphragm 69. Diaphragm 69 is a relatively thin disc member located in the transverse plane of bottom wall 67. The opposite end of the container 64 is closed with a transverse seal 71.

Container 64 is preferably made of a deformable lead alloy having good moisture and vapor barrier properties. Other deformable material having good moisture and vapor barrier properties can be used to fabricate the container. These properties are important to prevent moisture and vapor sensitive materials from polymerizing or setting up during storage periods. The material of the container is also chemically inert to the fluid stored in the container.

Located within the container 64 is a longitudinal needle 73. Needle 73 is a hollow member terminating in an inclined end having a point 74 located adjacent the inside of diaphragm 69. The opposite end of needle 73 is attached to a circular head 76. As shown in FIGS. 4 and 5, needle 73 has a longitudinal passage 77 extended through the pointed end of the needle. The side wall of needle 73 has a hole 78 to provide for the flow of liquid from the container through the needle. Needle 73 can have a plurality of holes or an enlongated slot to provide for the flow of fluid through the needle.

The chamber 61 is closed with a plunger or movable member 79. A portion of the movable member fits into the chamber and has outwardly directed ribs 81 and 82 extending into longitudinal grooves 83 and 84 in the inside portions of the cylindrical side wall 58. The ribs 81 and 82 hold the plunger 79 in assembled relation with the body and guide the body linearly into the chamber 61. Plunger 79 has an inwardly open recess 86 for accommodating the outer end of container 64. The bottom central portion of recess 86 has a cavity 87 providing a space for the sealed top 71. Plunger 79 can be removed from the side wall 58 enabling the container 64 to be removed from the chamber and replaced with a new container.

Referring to FIG. 6, the dispensing unit 51 is operated by moving the plunger 79 into the chamber 61. This is accomplished by applying a force on the outer end of plunger 79 in the direction of the arrow 88. The first and second fingers are placed under the ears 62 and 63. The thumb is used to apply force to the plunger 79. The needle 73 will be moved through the diaphragm 69. The fluid within container 64 will be placed under pressure and forced through the hole 78 along passage 77 and into the tube 49. The tube 49 carries the fluid up into the uterine cavity 27. The fluid is discharged from the end 54 and flows along the inner wall of the fundus into the canals 36 and 37 of the Fallopian tubes. Pressure is applied to plunger 79 until all of the fluid in the container 64 is dispensed therefrom. The sleeve member 39 being in engagement with the inner wall of the fundus limits the amount of fluid that can collect on the inner wall.

The dispensing unit 51 is a disposable item that contains a single dosage or unit of a drug or fluid. The dispensing unit can be used as part of a syringe to inject drugs into a body. The tube 49 can be replaced with a tubular needle which is placed on the outwardly directed tubular member 68. Tubular member 68 may contain threads to releasably hold the needle. Member 68 can be releasably or permanently attached to an enlongated delivery tube.

Referring to FIGS. 7, 8 and 9, there is shown a modification of the dispensing unit, indicated generally at 100, operable to discharge fluid, as drugs, under pressure into a tube or hypodermic needle. Tube 101 can be one of the delivery tubes of the catheter 21. Dispensing unit 100 has a body or housing 102 comprising a cylindrical side wall 103 joined to a flat end wall 104. Side wall 103 surrounds a cylindrical chamber 106 having an open end opposite end wall 104. Oppositely directed ears 107 and 108 are secured to the open end of the side wall 103.

Located within chamber 106 is a container or ampulla indicated generally at 109 for storing fluid, as drugs, tissue adhesive, water, air, gas, semi-fluids, and the like. Container 109 is a collapsible structure having a cylindrical side wall 111 and a bottom wall 112. Bottom wall 112 is located in flat surface engagement with the inside surface of end wall 104. The center portion of bottom wall 112 has a longitudinal tubular member 113. A portion of tubular member 113 extends through a hole 114 in bottom wall 112. Member 113 has an outwardly projected portion 113A and an inwardly directed portion 113B. The mid-portion of tubular member 113 has a transverse diaphragm or disc 116 closing the passage through the tubular member 113. The opposite or top end of the container is closed with a folded seal 117, thereby moisture and vapor closing the fluid in the container 109. A longitudinal needle 118 is located in the container 109. Needle 118 has a point 119 located in the upper or inner portion of the tubular member 113. The opposite end of needle 118 is attached to a transverse head 121. Head 121 is located adjacent the inside of the top wall of the container 109. As shown in FIG. 8, needle 118 is a generally U-shaped cross section. One side of the needle is open to the fluid in the container. This allows the fluid to flow longitudinally along the container past the point 119 when the point pierces the diaphragm 116. The needle can be a longitudinal tubular member having one or more holes providing access to the passage in the needle, as shown by needle 73 in FIG. 6.

A plunger 122 closes the open end of the housing 102. Plunger 122 has a pair of diametrically opposite ribs or projections 123 and 124. The ribs 123 and 124 are located in longitudinally extended grooves 126 and 127 in the inside of side wall 103 of the housing to guide the longitudinal movement of the plunger into the housing. The inner face of plunger 122 has an annular recess 128 to accommodate portions of the container when the plunger 122 is moved into the chamber 106. The center portion of plunger 122 has a cavity 129 for accommodating the seal 117 of the container.

In use, referring to FIG. 9, force is applied to plunger 122 in the direction of arrow 121. This moves the plunger 122 into the chamber 106. The plunger 122 collapses the container 109 and moves the needle through the diaphragm 116. As soon as the point 119 of the needle penetrates the diaphragm 116, the fluid within container 109 can flow through the needle 118 into the tube or receiver 101. Fluid will continue to flow through the needle 118 as long as force is applied to the plunger 122. Plunger 122 can be moved into chamber 106 until the head abuts against the inner portion of tubular member 113.

Referring to FIGS. 10 and 11, there is shown a modification of the needle and container arrangement. The bottom portion of container 132 has a generally flat end wall 133. The mid-portion of the end wall has a longitudinal tubular member 134. The tubular member 134 has an outwardly directed outer portion 134A and an inwardly projected inner portion 134B. The mid-portion of the tubular member 134, in general alignment with the end wall 133, has a diaphram or disc 136. A needle indicated generally at 137 is longitudinally aligned with the passage in the tubular member 134. Needle 137 has a cone-shaped head 138 terminating in a point. Head 138 is connected to an elongated shank 139. As shown in FIG. 11, when the needle 137 is moved in the direction of arrow 141, the head 138 punctures the diaphragm 136. The hole in the diaphragm 136 is larger than the shank 139 allowing the fluid in the container to flow past the diaphragm 136 into the discharge portion of the tubular member 134. The outer portion 134C of the tubular member has threads 142 adapted to receive a female threaded member, as a nut or sleeve, of a fluid receiving apparatus. Other types of connections can be used to couple the tubular member 124 to the fluid receiving apparatus.

Referring to FIGS. 12 and 13, there is shown a fluid dispensing container or ampulla indicated generally at 143. The container has a cylindrical side wall 144 surrounding a chamber 145 for storing fluid, as drugs, tissue adhesive, water and the like. Wall 144 is made of non-collapsible material. A generally flat transverse end wall 146 is integral with one end of side wall 144. The center portion of end wall 146 has an elongated longitudinal tubular member 147. Tubular member 147 has an outer portion 147A extended outwardly from end wall 146 and an inner portion 147B projected into chamber 145. The mid-portion of tubular member 147 is closed with a diaphragm 148. Diaphragm 148 is located in transverse alignment with the end wall 146 and is of a material than can be pierced with a needle.

An elongated longitudinal needle 149 is located within chamber 145. Needle 149 has a forward end located within the passage of inner portion 147B and terminates in a point 151. The opposite end of needle 149 is attached to a transverse head 152. The head 152 has an annular outer peripheral surface which forms a seal 153 with the adjacent inner wall of the side wall 144. The outer peripheral surface of the head 152 is in sealing frictional fit with the inner surface of side wall 144 so as to prevent moisture, air or other substances from entering chamber 145. Needle 149 has a generally U-shaped cross section as shown by needle 118 in FIG. 8. Alternatively, needle 149 can be a tubular member having one or more side holes to provide a passage for the movement of fluid in chamber 146 out the end of needle 149. The needle can also have the shape of needle 137, as shown in FIGS. 10 and 11. Other shapes and structures can be used to permit the flow of fluid along the needle through the diaphragm once the diaphragm has been pierced by the point of the needle.

In use, the head 152 is moved into the chamber 145 in the direction of arrow 154 shown in FIG. 13. The point 151 of the needle will penetrate and pierce the diaphragm 148. The fluid in chamber 145 is forced along the needle through the pierced diaphragm and discharged via the outer portion 147A of the tubular member.

Figure 19:
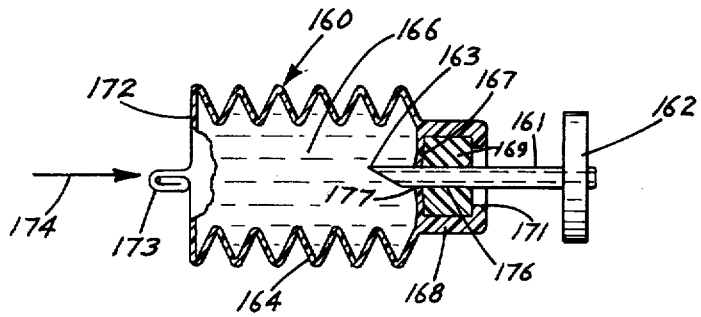
FIG. 19 is a sectional view similar to FIG. 16 showing the container in assembled relation with the needle.

Referring to FIGS. 14 and 19, there is shown a container or ampulla indicated generally at 160 for storing a fluid, as a drug, liquid tissue adhesive, semi-liquid material or a gas. Container 160 is located in longitudinal alignment with a tubular needle 161. Needle 161 is secured to a generally transverse base 162 and has a point or sharp edge 163 at its forward end. Base 162 is mounted in a housing (not shown) to fix the position of the needle 161.

Container 160 is a one-piece body having a continuous side wall 164. Side wall 164 has an accordion shape and is of a cylindrical configuration and surrounds a chamber 166 for storing the fluid. The forward end 167 is closed with a diaphragm or cylindrical disc member comprising an end wall 167. An outwardly directed longitudinal sleeve 168 is attached to the outer peripheral edge of the end wall 167 forming an extension of the container. A disc or pad 169 of resilient material, as sponge rubber, plastic foam or the like, is located within sleeve 168 and covers the end wall 167. Sleeve 168 has a rolled outer edge or bead 171 holding the pad within the sleeve 168.

Figure 17:
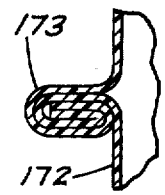
FIG. 17 is an enlarged sectional view of the sealed end of the container.

The rear end of the container is closed with an end wall 172. End wall 172 has a transverse seam 173 closed to moisture and vapor to seal the container. As shown in FIG. 17, the seam 173 has lapped and in-turned edges that are sealed together. The container is made of a material having moisture and vapor impervious properties. Preferably the material is a deformable lead alloy which is chemically inert to the fluid stored in the container. Other deformable materials having good moisture and vapor barrier properties can be used to form the container. These properties are essential to prevent moisture and vapor sensitive materials from setting up or polymerizing during lengthy storage periods. For example, the cyanoacrylate monomer is extremely sensitive to moisture and vapor. It must be stored in a sealed container which does not allow ingress of moisture and vapor. The monomer will set up in a short period of time when exposed to moisture, including the moisture of tissues.

In use, force is applied to the end wall 172 in the direction of arrow 174. This force moves the container 160 into operative engagement with needle 161. The force will also collapse the side wall 164 and apply sufficient force to the container whereby the needle 161 will cut through or pierce both the pad 169 and the end wall 167. Pad 169, being made of resilient elastic material, will be formed with a hole 176 in tight sealing engagement with the outer peripheral surface of needle 161. Needle 161 will also make a hole 177 in the end wall 167. The needle 161, being a hollow tubular member, provides a passage for the flow of fluid from chamber 166 into a fluid receiver such as the tube of the dispensing catheter.

Figure 20:
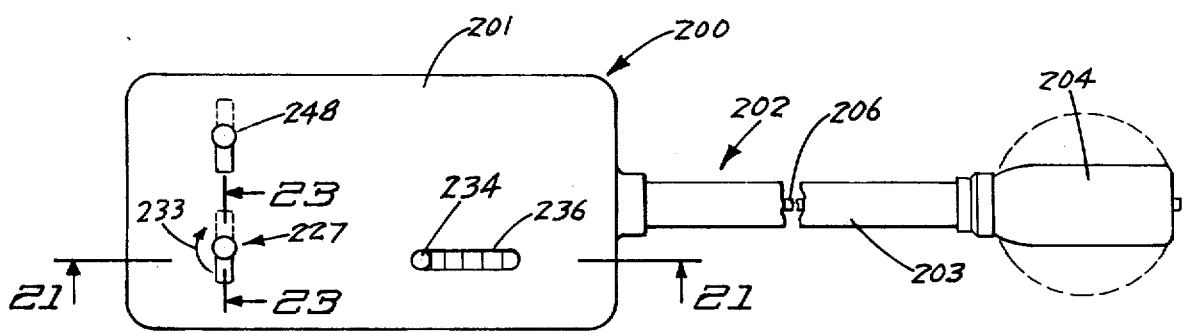
FIG. 20 is a top plan view of a modified dispensing catheter of the invention.
Figure 22:
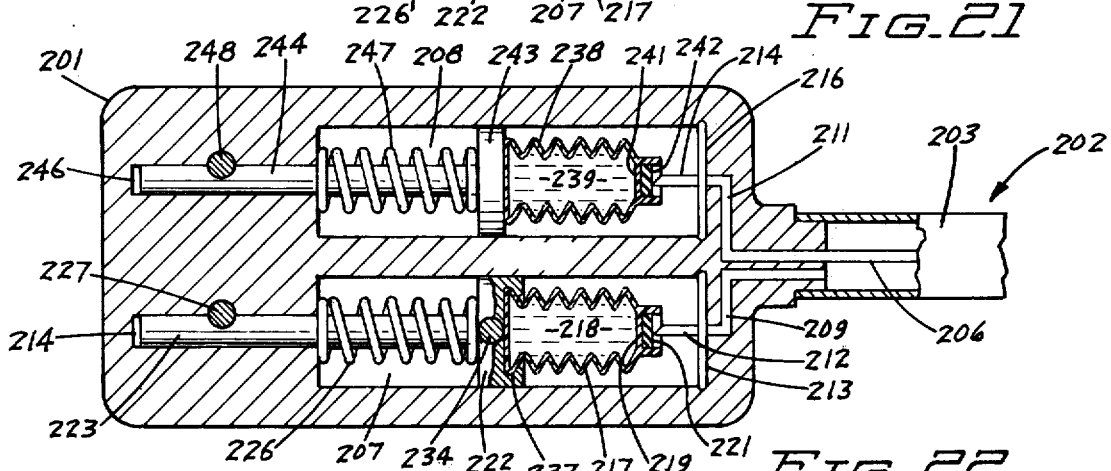
FIG. 22 is a sectional view taken along the line 22—22 of FIG. 21.

Referring to FIG. 20, there is shown a catheter dispenser having a dispensing unit indicated generally at 200 attached to an elongated balloon catheter 202. The dispensing unit has a body or housing 201 attached to an elongated linear tube 203 of the catheter. Tube 203 can be an integral extension of the body or releasably connected to the body 201. The outer end of the catheter has an expandable sleeve member or balloon 204 adapted to confine fluid, as water or a gas, to enlarge the expandable sleeve member 204. As shown in FIG. 22, a second smaller tube 206 is located within the tube 203. Tube 206 extends the entire length of the tube 203 and has an outlet opening 205 at the outer end whereby fluid can be discharged from the catheter. The outer end of tube 203 can be recessed to insure the flow of fluid from outlet opening 205.

The body 201, as shown in FIG. 22, has a pair of longitudinally extended chambers 207 and 208. Chambers 207 and 208 are located side-by-side in a generally horizontal plane. The chambers can be located in a generally vertical plane. A passage 209 connects the chamber 207 with the passageway of tube 203. A similar passage 211 connects the chamber 208 with the passage in tube 206. A short tubular needle 212 extends longitudinally into passage 207. Needle 212 is attached to a transverse space 213 positioned at the end of chamber 207 having the passage 209. The outer peripheral edge of base 213 is located in a groove in the housing to fix the position of the base and needle relative to the passage 207. The needle 212 has a passage in alignment with passage 209 so that fluid flows through the needle into the passage 209.

A second tubular needle 214 is located longitudinally in passage 208. Needle 214 is attached to a base 216 located at the end of chamber 208 adjacent the passage 211. The outer peripheral edge of base 216 is located in grooves in the housing 201 to fix the position of the base and needle relative to passage 208. The passage of needle 214 is aligned with the passsage 211 so that the fluid can flow through the needle and into passage 211.

A container or ampulla 217 having a chamber 218 for fluid, as drugs, water, or other material, is located in chamber 207. Container 217 has an end or diaphragm 219 facing the needle 212. A pad 221 of resilient cushioning material is located between diaphragm 219 and the pointed end of needle 212. A plunger 222 is attached to the opposite end of container 217. A suitable dovetail or tongue and groove 237 can be used to connect the container to the plunger. Other types of connections can be used to attach the container to the plunger. A longitudinal rod 223 is connected to plunger 222 and extended into a bore 224 in the housing 201. A coil spring 226 is positioned around rod 223 and engages the housing 201 and the plunger 222 to bias the plunger toward the needle 212.

Figure 18:
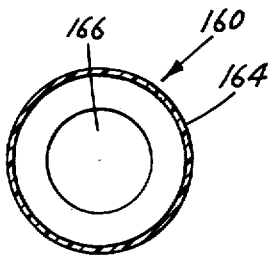
FIG. 18 is a sectional view taken along line 18—18 of FIG. 14.
Figures 23, 24, 25:
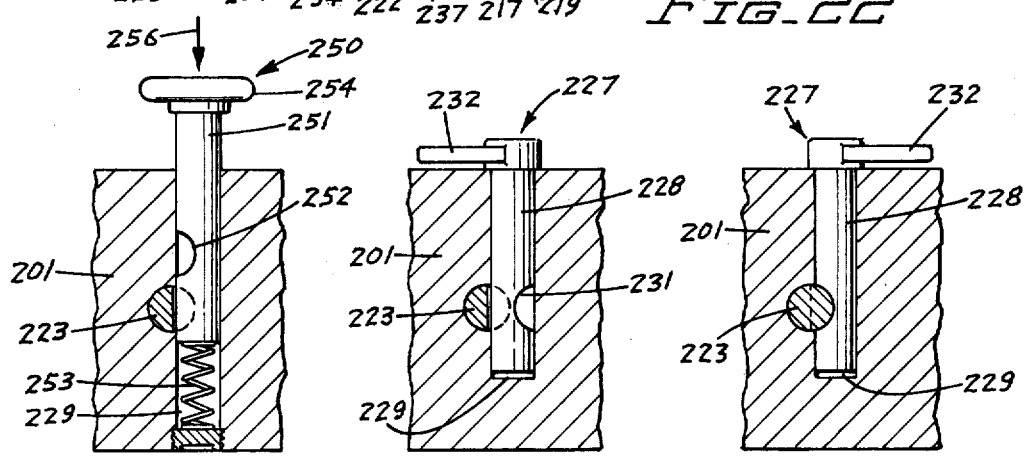
FIG. 23 is an enlarged sectional view taken along the line 23—23 of FIG. 20.
FIG. 24 is a sectional view similar to FIG. 23 showing the lock in the release position.
FIG. 25 is a sectional view similar to FIG. 23 showing a modification of the lock.

A releasable lock 227 engages the lock 222 to hold the plunger 221 in a cocked position whereby the diaphragm 219 is held from the needle 212. Referring to FIGS. 23 and 24, releasable lock 227 comprises a cylindrical member or body 228 extended downwardly into a hole 229 in housing 201 through a cutout or groove 230 in rod 223. The body 228 has a semicircular cutout 231 in alignment with rod 223. The upper or exposed end of the body 228 has a handle 232. The handle 232 is movable in the direction of arrow 233 shown in FIG. 20 to move the cutout 231 in registration with the rod 223. When the cutout 231 is in registration with rod 223, as shown in FIG. 18, the rod is free to move. The spring 226 will bias plunger 222 toward the needle 212. This moves the container 217 and the diaphragm 219 into the needle 212. The pointed end of the needle will pass through the pad 221 and puncture the diaphragm 218. The needle 212 will form a seal with the diaphragm 219 whereby the fluid in chamber 218 will flow through the needle, passage 209 and into the passage of catheter tube 203. The biasing force of spring 226 will force substantially all of the fluid in chamber 218 through the needle 212.

Figure 21:
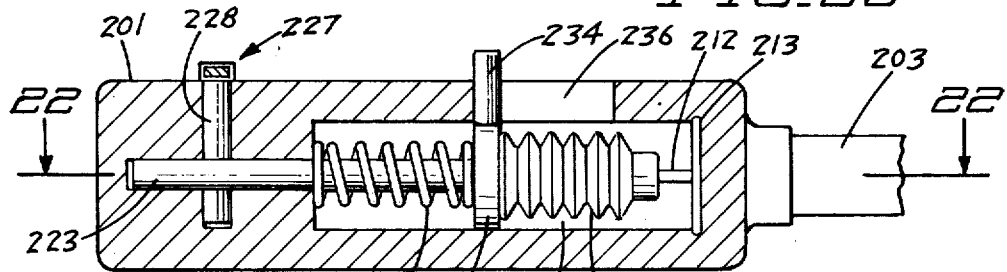
FIG. 21 is an enlarged sectional view taken along the line 21—21 of FIG. 20.

An upwardly directed finger 234, shown in FIG. 21, is attached to the plunger 222. The finger 234 extends through a longitudinal slot 236 in the housing 201. The upper end of finger 234 is enlarged so that it can be gripped. The plunger 222 and container 217 have cooperating connections such as a dovetail connection 237, shown in FIG. 22. When force is applied to finger 234, the plunger 222 can be moved in a reverse direction, expanding the container 217. This withdraws the fluid from the catheter, decreasing the size of the expandable member 204. The plunger 222 can be moved until the lock 227 can be moved to fix the position of the plunger 222 in the housing. Other types of retraction structure can be used to withdraw and expand the container 217 to relieve the fluid from the expandable member 204.

A container or ampulla 238 is located in chamber 208 adjacent the needle 214. Container 238 has a chamber 239 for storing drugs, tissue adhesive and other materials. Container 238 has an end or diaphragm 241 spaced from the pointed end of needle 214 with a resilient pad 242. Some drugs that are moisture and vapor sensitive require a container made of material having good moisture and vapor barrrier properties. Preferably a deformable lead alloy is used to make this type of container. Other deformable material having good moisture and vapor barrier properties can be used to fabricate the container. These properties are important to prevent moisture and vapor sensitive materials from polymerizing or setting up during storage periods. The material of the container is also chemically inert to the fluid storage in the container. Located adjacent the opposite end of container 238 is a plunger 243. A longitudinal rod 244 attached to plunger 243 extends into a bore 246 in housing 201. A spring 247 located in chamber 208 engages the housing 201 and plunger 243 to bias the plunger toward the needle 214. The rod 244 is held with a releasable lock 248. Lock 248 is identical to lock 227. It is operated by moving the handle of the lock to the dotted line position, as shown in FIG. 14. This releases the rod 214 whereby the spring 247 will bias the plunger to a forward direction, moving the diaphragm 241 toward the needle 214. The pointed end of needle 214 will pierce the diaphragm 241, thereby providing a fluid connection between the chamber and the passage 211 leading to the tube 206. The diaphragm will be located in sealing relation with respect to the needle whereby the fluid in chamber 239 of container 238 will be forced by the biasing action of the spring 247 through the needle 214, the passage 211 and the passage of tube 206.

Body 201 has doors or closure members closing openings into the chambers 207 and 208 whereby the containers 217 and 238 can be removed and replaced. Other types of containers as herein disclosed can be inserted into the chambers.

Referring to FIG. 25, there is shown a modification of the releasable lock, indicated generally at 250. Lock 250 has a body or rod 251 having a cylindrical cutout 252. The rod 223 attached to the plunger has a similar cutout. A spring 253 located in the base of bore 229 biases the body 251 in an upward direction. The upper end of body 252 is attached to a head 254.

In use, body 251 has a portion located in the groove or recess in the side of the rod 223 to hold the rod in the cocked position, as shown in FIG. 22. The rod 223 is released by pushing head 254 in a downward direction, as indicated by arrow 256, until the cutout 252 is aligned with rod 223. This releases the holding action on rod 223 whereby the spring 226 can move the rod in a forward direction, forcing the diaphragm 219 into engagement with the needle 212.

Referring to FIGS. 26, 27, 28 and 29, there is shown a further modification of a dispenser catheter of the invention indicated generally at 300 for discharging fluid, as drugs, tissue adhesive, and the like, into the uterine cavity. The dispenser catheter 300 has a dispensing unit 301 and elongated tubular catheter 302. Dispensing unit 301 has a body 303 attached to elogated tube 204 of the catheter. Tube 304 can be releasably connected or permanently fixed to body 303. Mounted on the end of tube 304 is an expandable sleeve member or balloon 305. Bands 306 clamp the ends of the sleeve member 305 to the tube 305. Sleeve member 304 is an elastic sheet member, of relaxed rubber, plastic or like materials. When the sleeve member 305 is expanded in the uterine cavity it applies uniform outward pressure on the uterine wall. The expanded sleeve member 305 prevents the drugs injected into the uterine cavity from contacting substantial portions of the uterine wall and flowing out of the uterine cavity. Holes 307 in the end of tube 304 provide the passageway for the fluid, from within the tube 304 into the area surrounded by the sleeve member 305 to expand the sleeve member 305. An elongated small tube 308 is located within tube 304. Tube 304 has a discharge end 309 at the outer end of tube 304.

Body 303 has a pair of side-by-side chambers 311 and 312. The chambers 311 and 312 extend in a longitudinal direction and are located in a common horizontal plane. The chambers can be located in a common vertical plane whereby one chamber is positioned over the other chamber. A passage 313 connects the chamber 311 with the tube 304. In a similar manner, a passage 314 connects chamber 312 with the tube 308.

A first plunger 316 is movably positioned in first chamber 311. A rearwardly directed rod 317 is attached to plunger 316. A second plunger 318 is movably located in chamber 312. A rod 319 is secured to the plunger 318 and extends in a rearward direction generally parallel to the rod 317. A trigger assembly or actuator indicated generally at 320 is mounted on the rear portion of the housing adjacent the rear end of rods 317 and 319.

Trigger assembly 320 has a lever 321. The mid-portion of lever 321 has a hole accommodating a transverse pivot pin 322. Pivot pin 322 is anchored in a downwardly extended handle or pistol grip 323 secured to the rear portion of the body 303. Lever 321 has a transverse head 324. A spring 325 engages the body 303 and upper end of lever 321 to bias the lever in the rear or cock position. The forward portion of head 324 is in sliding engagement with the ends of rods 317 and 319.

Referring to FIGS. 29 and 30, head 324 has a longitudinal passage 326 for accommodating rod 319. A transverse bore 327 opens into passage 326. Slideably disposed in bore 327 is a pin 328. Pin 328 has a reduced diameter neck 329 attached to an enlarged head 331. A spring 332 engages the head 331 and a plug 333, closing the end of bore 327. Spring 332 biases the pin 328 into the passage 326. Rod 317 has a rearwardly directed finger 334. When the rod 317 is in the rearward or cocked position, the finger 334 is located behind the head 331 and functions as a stop to prevent movement of pin 328 into the passage 326. Returning to Figure 27, rod 317 has a notch or slot 336 in the upper portion thereof. The slot 336 cooperates with lock 337 to hold the rod 317 in the dispensed or in position. Lock 337 comprises a movable pin 338 located in a passage surrounded by a boss 339. The pin 338 has a head 341 located above the body 303 so that it can be gripped to release the lock. The forward portion of the pin carries a C-ring or clamp ring 342 providing a stop for a spring 343. Spring 343 is located concentrically around the pin and engages a portion of the body 303 to bias the pin 338 toward the rod 317. When the rod 317 has been moved to the "in" position, the pin 338 in the "in" position. The rod 319 has a slot 344. A lock 346 on body 303 holds the pin in the "in" position. The lock 346 is identical to the lock 337.

Returning to FIG. 30, whenthe lever 323 has been actuated, the rod 317 will be held in the "in" position by lock 337. The rod 319 is not moved because the head 324 will move relative to the rod 319 as the rod 319 moves through the passageway 326. When the head 324 is returned by spring 325 to its initial rearward posistion, the pin 328 will be biased by spring 332 into the passage 326. The second actuation or movement of the lever 321 toward the handle 323 will move the rod 319 in the forward direction.

Referring to FIG. 28, a first container or ampulla indicated generally at 350 is located in chamber 311. A forwardly directed needle 351 mounted on a transverse base 352 is located at the forward end of chamber 311. Needle 351 is a hollow member in fluid communication with the passage 313.

A second container or ampulla, indicated generally at 353, is located in passage 312. The forward end of passage 312 has a longitudinally extended needle 354 mounted on a transverse base 356. Needle 354 is a hollow tubular member having a passsage in fluid communication with the passage of the tube 314. The container 353 is an elongated cylindrical member of glass, plastic or the like having a head 357. The head has a rubber plug (not shown) in alignement with needle 354. Slideably positioned within the container is a plunger or piston 358 confining fluid 359 in the container. The plunger 318 is slideably positioned within the container and engageable with the piston 358. On movement of plunger 318 in a forward direction, the head 357 will be driven through needle 354, thereby providing a fluid communication between the chamber of the container 353 and the tube 314. The piston 358 will be moved in a forward direction to drive the fluid from the container. The fluid can be a drug, tissue adhesive, or semi-fluid material for treating and occluding the canals of the Fallopian tubes.

Container 350, shown in FIG. 31, has a cylinder 361 for storing fluid 362, as drugs, water or the like. The forward end of cylinder 361 has a head 363 having a passage closed with a plug 364. The open end of cylinder 361 is closed with a plunger 366 carrying a piston 367. The rear portion of plunger 366 has an outwardly directed flange 368 engageable with a spring 369. The forward end of spring 369 engages an annular seat 371 on the cylinder 361 to bias the plunger in an outward direction or out of the cylinder 361. Plunger 366 has a central longitudinal bore 372 slideably accommodating an actuator rod 373. Rod 373 has an axial bore accommodating a compression spring 374 to provide a yieldable link between rod 373 and the plunger 366.

The plunger 316 attached to the rod 317 engages the end of rod 376. On movement of plunger 316 in a forward direction, spring 374 will be intially compressed applying a uniform pressure on plunger 366. The cylinder 361 will be moved in a forward direction whereby needle 351 will pierce plug 364, providing fluid communication betwen the container and the passage 313. The continued movement of the plunger 316 will drive the piston 367 toward the plug 364, thereby dispensing the fluid from the cylinder 361. The dispensed fluid will flow through the tube 304 and into the sleeve member 305 via holes 307 to expand the sleeve member 305, as shown in broken lines in FIG. 22. Sleeve member 305 will expand with a uniform pressure so as to fill the uterine cavity and exert uniform pressure on the inside wall of the cavity. The pressure of the sleeve member 305 on the cavity wall will be unifrom regardless of the size of the uterine cavity.

Body 303 has doors or closure members closing openings into the chambers 311 and 312 whereby the containers 350 and 353 can be removed and replaced. Other types of containers as disclosed herein can be inserted into the chambers.

In use, the dispensing catheter performs a method of introducing a material, as a drug, tissue adhesive, contraceptive gel and like materials, into the canals of the Fallopian tubes. The method includes the introduction of the an elongated catheter 302 with the sleeve member 305 in the contract-position through the cervical opening into the uterine cavity. Sleeve member 305 is expanded with fluid under pressure to fill the uterine cavity and apply uniform pressure on the inside of the uterine wall. The fluid under pressure is delivered to sleeve member 305 via the passage in the tube 304. The actuator 320 is moved in a forward direction to force the plunger 316 in a direction to move the container 350 into operative engagement with the needle 351. The needle 351 will puncture the plug 364 whereby the fluid 362 will flow via the passage in tube 304 to expand sleeve member 305. The sleeve member, being a sheet of flexible, elastic, rubber or similar material, has a low surface tension and applies a uniform expansion force to the inside of the uterine wall. This effects a relatively tight seal and fit, enabling the same catheter construction to be used on all types of primate female, regardless of the size of the uterine cavity.

The material under pressure is then dispensed into the uterine cavity between the expanded sleeve member and the fundus of the uterus. The material, being under pressure, moves toward and into the canals of the Fallopian tubes. The expanded sleeve member, being located against the fundus wall, aids the movement of the material toward the canals of the Fallopian tubes. The material can be a fluid tissue adhesive which will flow into the canals. The moisture in the tissue of the canals will polymerize or set the tissue adhesive and thereby block or occlude the canals. The fluid confined by the sleeve member is drained to contract the sleeve member. The catheter is then withdrawn from the uterine cavity.

While there have been shown and described several preferred embodiments of the dispensing catheter and fluid container, as well as the method of introducing material into the canals of the Fallopian tubes, it is understood that variations and changes in the structures and methods can be made by those skilled in the art without departing from the spirit of the invention. The invention is defined in the following claims.

The embodiments of the invention in which an exclusive property or privilege is claimed are defined as follows:

1. A dispensing catheter comprising: housing means having a first chamber and a second chamber separated from the first chamber for storing fluids, means having a first passage connected to the first chamber and a second passage connected to the second chamber for receiving fluid from the respective chambers, means operable to first dispense fluid from the first chamber into the first passage and to subsequently dispense fluid from the second chamber into the second passage, said means operable to first dispense fluid from the first chamber including a plunger located in the first chamber and biasing means operable to move the plunger into the first chamber and releasable lock means to hold the plunger in a non-fluid dispensing position against the force of the biasing means, said lock means being movable to a position whereby the biasing means moves the plunger into the first chamber.

2. The dispensing catheter of claim 1 wherein: the means having a first passage is an elongated tube and an expandable sleeve member mounted on the outer end of the tube, said sleeve member being expanded in response to the discharge of fluid into the firsts passage.

3. The dispensing catheter of claim 2 wherein: the sleeve member is an elastic relaxed rubber member.

4. The dispensing catheter of claim 2 wherein: the second passage has an outlet opening at the end of the tube having the sleeve member.

5. The dispensing catheter of claim 1 including: first container means storing fluid located in the first chamber and second container means storing fluid located in the second chamber, and means for fluidly coupling the first container means with the first passage and second container means with the second passage.

6. The dispensing catheter of claim 5 wherein: the means for fluidly coupling include needle means for piercing the container means in response to operation of the means operable to dispense fluid from the chambers.

7. The dispensing catheter of claim 1 wherein: the means operable to dispense fluid from the second chamber includes a second plunger located in the second chamber, and second biasing means operable to move the second plunger into the second chamber and second releasable lock means to hold the second plunger in a non-fluid dispensing position against the force of the second biasing means, said second lock means being movable to a position whereby the second biasing means moves the second plunger into the second chamber.

8. The dispensing catheter of claim 7 including: first container means storing fluid located in the first chamber and second container means storing fluid located in the second chamber, and means for fluidly coupling the first container means with the first passage and second container means with the second passage.

9. The dispensing catheter of claim 8 wherein: the means for fluidly coupling include needle means for piercing the container means in response to operation of the means operable to dispense fluid from the chambers.

10. A dispensing apparatus comprising: housing means having a first chamber and a second chamber separated from the first chamber for storing fluids, means having a first passage connected to the first chamber for receiving fluid from the first chamber and a second passage connected to the second chamber for receiving the fluid from the second chamber, means operable to first dispense fluid from the first chamber into the first passage and to subsequentially dispense fluid from the second chamber into the second passage, said means operable to dispense fluid from the chambers including a first movable means having a portion located in the first chamber and a second movable means having a portion located in the second chamber, and actuator means havng a member locatable in a first position to engage the first movable means whereby operation of the actuator means moves only the first movable means to dispense fluid from the first chamber, said member alternatively locatable in a second position to engage the second movable means whereby operation of the actuator means moves the second movable means to dispense fluid from the second chamber.

11. The dispensing apparatus of claim 10 including: lock means cooperating with the first movable means to hold the first movable means in its dispensed position.

12. The dispensing apparatus of claim 10 including: first container means storing fluid located in the first chamber and second container means storing fluid located in the second chamber, and means for fluidly coupling the first container means with the first passage and second container means with the second passage.

13. An apparatus for sequentially dispensing a first fluid and a second fluid comprising: a housing having a first chamber and a second chamber, first container means storing a fluid located in the first chamber, second container means storing a fluid located in the second chamber, first needle means operable to puncture the first container means, second needle means operable to puncture the second container means, means having a first passage for receiving fluid from the first container means, and a second passage for receiving fluid from the second container means, first movable means operable to cause the first needle means to pierce a portion of the first container means whereby fluid flows from the first container means to the first passage and second movable means operable to cause the second needle means to pierce the second container means whereby fluid from the second container means flows to the second passage and actuator means operable to sequentially move the first movable means and the second movable means whereby the fluid from the first container is dispensed before the fluid in the second container is dispensed.

14. The apparatus of claim 13 including: lock means for holding the first movable means in the fluid dispensed position.

15. The apparatus of claim 13 wherein: the actuator means has a member located in a first position to engage the first movable means and in a second position to engage the second movable means.

16. The apparatus of claim 13 including: lock means for holding the first movable means in the dispensed position, said actuator means having a member held in a first position by the first movable means and movable to a second position wherein the member is engageable with the second movable means, said member beig held in the first position by the first movable means until the first movable means is locked.

17. The apparatus of claim 13 wherein: the actuator means includes a lever pivotally mounted on the housing, said member movably mounted on a portion of said lever.

18. The apparatus of claim 13 wherein: the means having a first passage and a second passage includes an elongated tube and an expandable sleeve means for receiving and collecting the fluid dispensed from the first container means.

19. The apparatus of claim 18 wherin: the second passage has an outlet opening at the end of the tube having the sleeve member.

20. An instrument for use in performing female sterilization comprising: means for containing material for occluding the canals of the Fallopian tubes, dispensing means having a portion positionable in the uterine cavity of the female and operable to move the material from the means for containing material to the uterine caity and from the uterine cavity into the canals of the Fallopian tubes thereby sterilizing the female, said dispensing means including a housing having a first chamber and a seconnd chamber, first container means storing a fluid located in the first chamber, said means for containing material comprising a second container means storing said material located in the second chamber, first needle means operable to punch the first container means, second needle means operable to punch the second container means, means having a first passage for receiving fluid from the first container means and a second passage for receiving fluid from the second container means, first movable means operable to cause the first needle means to pierce a portion of the first container means whereby fluid flows from the first container means to the first passage and second movable means operable to cause the second needle means to pierce the second container means whereby fluid fromthe second container means flows to the second passage, and actuator means operable to sequentially move the first movable means and the second movable means whereby the fluid from the first container is dispensed before the fluid in the second container is dispensed.

21. The instrument of claim 20 including: lock means for holding the first movable means in the fluid dispensed position.

22. The instrument of claim 20 wherein: the actuator means has a member located in a first position to engage the second movable means.

23. The apparatus of claim 20 includng: lock means for holding the first movable means in the dispensed position, said actuator means having a member held in a first position by the first movable means and movable to a second position wherein the member is engageable with the second movable means, said member being held in the first position by the first movable means until the first movable means is locked.

24. The apparatus of claim 20 wherein: the actuator means includes a lever pivotally mounted on the housing, said member movably mounted on a portion of said lever.

25. The apparatus of claim 20 wherein: the means having a first passage and a second passage includes an elongated tube and expandable sleeve means for receiving and collecting the fluid dispensed from the first container means.

26. The apparatus of claim 20 wherein: the second passage has an outlet opening at the end of the tube having the sleeve member.

27. Apparatus for dispensing substance means into the Fallopian tubes of a female body comprising: first and second means adapted to be placed in a uterine cavity; the first means including means for selective expansion for substantially completely filling the uterine cavity and making firm engagement with the inner wall of the uterine cavity including the fundus and the cornual areas, all regardless of the size of the uterine cavity; and the second means including means for providing a substance passage into the uterine cavity.

28. The apparatus of claim 27 in which: the means for expansion comprises material means sufficiently flexible to generally conform to the shape of the uterine cavity when expanded to substantially completely fill the uterine cavity.

29. The apparatus of claim 28 in which: the material means comprises rubber.

30. The apparatus of claim 28 in which: the material means comprises plastic.

31. The apparatus of claim 27 in which: the means for expansion comprises flexible sleeve means.

32. The apparatus of claim 31 in which: the sleeve means comprises material means sufficiently flexible to generally conform to the shape of the uterine cavity when expanded to substantially completely fill the uterine cavity.

33. The apparatus of claim 32 in which: the material means comprises rubber.

34. The apparatus of claiIm 32 in which: the material means comprises plastic.

35. The apparatus of claim 31 in which: the sleeve means comprises a baloon.

36. The apparatus of claim 32 in which: the sleeve means comprises a balloon.

37. The apparatus of claim 27 in which the means for providing a substance passage includes a passage exit adapted to be adjacent the uterine fundus when the second means is in the uterine cavity.

38. The apparatus of claim 27 including: third means connected to the first and second means for inserting the first and second means into the uterine cavity; the third means including first and second passage means; the first passage means connected to the firsts means; the second passage means connected to the second means; and the first and second passage means constructed to extend from the body when the first and second means are in the uterine cavity.

39. The apparatus of claim 38 including: expansion control means connected to the first passage means for selectively expanding the means for expansion from a point external to the body.

40. The apparatus of claim 38 includng: substance storage means connected to the second passage means for providing substance means to the means for providing a substance passage from a point external to the body.

41. The apparatus of claim 38 including: control means connected to the first and second passage means for sequentially expanding the means for expansion and providing substance means to the means for providing a substance passage from a point external to the body.

42. The apparatus of claim 41 in which: the means for providing a substance passage includes a passage exit adapted to be adjacent the uterine fundus when the second means is in the uterine cavity.

43. Apparatus for dispensing mateirals into the Fallopian tubes of a female body comprising: expandable sleeve means; catheter means; dispensing means connected to the sleeve means and the catheter means for insertion thereof into a uterine cavity; and the dispensing means including first means operable to expand the sleeve means to substantially completely fill the uterine cavity and make firm engagement with the wall of the uterus including the fundus and the cornual areas, all regardless of the size of the uterine cavity; and second means operable to dispense materials through the catheter means.

44. The apparatus of claim 43 in which: the sleeve means comprises a material sufficiently flexible to conform to the shape of the uterus when the sleeve means is expanded to substantially completely fill the uterine cavity.

45. The apparatus of claim 43 in which: the catheter means is constructed to have a material exit adjacent the uterine fundus when placed in the uterine cavity.

46. The apparatus of claim 43 in which: the first and second means are constructed to extend out of the body when the sleeve means and catheter means are in the uterine cavity.

47. The apparatus of claim 46 including: means connected to the first and second means for providing automatic sequential operation thereof.

48. Apparatus for dispensing materials into the Fallopian tubes of a female body comprising: catheter means havng first and second isolated passages; expandable balloon means connected to the first passage; fluid dispensing means connected to the first passage for selective expansion of the balloon means for selectively completely filling a uterine cavity and making firm engagement with the wall of the uterus including the funuds and the cornual areas, all regardless of the size of the uterine cavity; and material dispensing means connected to the second passage for dispensing selected materials into the uterine cavity to the forced into the Fallopian tubes.

49. The apparatus of claim 48 in which: the baloon means is of a material sufficiently flexible to conform to the shape of the uterus when the balloon means is expanded to substantially completely fill the uterine cavity.

50. The apparatus of claim 49 including: means connected to the fluid dispensing means and the material dispensing means for providing automatic sequential operation thereof.

* * * * *